US010925919B2

(12) United States Patent
Ishida et al.

(10) Patent No.: US 10,925,919 B2
(45) Date of Patent: Feb. 23, 2021

(54) AGENT FOR ACTIVATING ASTROCYTE GLUCOSE METABOLISM (71) Applicant: Kao Corporation, Tokyo (JP)

(72) Inventors: Keiko Ishida, Maoka (JP); Koichi Misawa, Utsunomiya (JP); Kohjiro Hashizume, Utsunomiya (JP)

(73) Assignee: Kao Corporation, Tokyo (JP)

( * ) Notice: Subject to any disclaimer, the term of this patent is extended or adjusted under 35 U.S.C. 154(b) by 151 days.

(21) Appl. No.: 16/068,408

(22) PCT Filed: Jan. 4, 2017

(86) PCT No.: PCT/JP2017/000023
§ 371 (c)(1),
(2) Date: Jul. 6, 2018

(87) PCT Pub. No.: WO2017/130638
PCT Pub. Date: Aug. 3, 2017

(65) Prior Publication Data
US 2019/0015469 A1   Jan. 17, 2019

(30) Foreign Application Priority Data

Jan. 28, 2016 (JP) .............................. JP2016-013957
Dec. 22, 2016 (JP) .............................. JP2016-248774

(51) Int. Cl.
A61K 36/82 (2006.01)
A61K 36/48 (2006.01)
A61K 36/00 (2006.01)
A61K 36/73 (2006.01)
A61K 36/87 (2006.01)
A61P 3/08 (2006.01)

(52) U.S. Cl.
CPC .............. A61K 36/82 (2013.01); A61K 36/48 (2013.01); A61K 36/73 (2013.01); A61K 36/87 (2013.01); A61P 3/08 (2018.01)

(58) Field of Classification Search
None
See application file for complete search history.

(56) References Cited

U.S. PATENT DOCUMENTS

2004/0253647 A1* 12/2004 Mathews ................ A61P 25/16
435/7.2
2010/0034764 A1  2/2010 Pecher et al.
2010/0222423 A1  9/2010 Frank et al.
2011/0159122 A1  6/2011 Frank

FOREIGN PATENT DOCUMENTS

| CN | 1370528 A | 9/2002 |
|---|---|---|
| CN | 101874530 A | 11/2010 |
| CN | 102613345 A | 8/2012 |
| CN | 102669345 A | 9/2012 |
| CN | 103087828 A | 5/2013 |
| CN | 103749919 A | 4/2014 |
| CN | 104322736 A | 2/2015 |
| CN | 105237598 A | 1/2016 |
| EP | 2 053 050 A1 | 4/2009 |
| EP | 2 161 026 A1 | 3/2010 |
| JP | H01-283227 A | 11/1989 |
| JP | H05-246866 A | 9/1993 |
| JP | H09-118626 A | 5/1997 |
| JP | 2002-532416 A | 10/2002 |
| JP | 2004-307443 A | 11/2004 |
| JP | 2007-297304 A | 11/2007 |
| JP | 2010-031010 A | 2/2010 |
| JP | 2011-520814 A | 7/2011 |
| JP | 2012-501990 A | 1/2012 |
| JP | 2013-514994 A | 5/2013 |
| JP | 2013-253072 A | 12/2013 |
| JP | 2014-118406 A | 6/2014 |
| JP | 2018-177748 A | 11/2018 |
| KR | 2007078527 A * | 8/2007 |
| WO | WO 00/35437 A2 | 6/2000 |
| WO | WO 2009/137818 A1 | 11/2009 |
| WO | WO 2011/075654 A1 | 6/2011 |

OTHER PUBLICATIONS

JP 1-283227 A (Yugen Kaisha Nonogawa Shojii), Nov. 14, 1989 (Nov. 14, 1989), claims 2, 5; p. 2, lower left column, lines 4 to 8, examples 1, 3 (also contained within the IDS) (Year: 1989).*
JP 1-283227 A (Yugen Kaisha Nonogawa Shojii), Nov. 14, 1989 (Nov. 14, 1989), claims 2, 5; p. 2, lower left column, lines 4 to 8, examples, 1, 3 (also contained in the IDS) (Year: 1989).*
Vickers (A Vaccine Against Azheimer's Disease, Drug Aging 2002: 19(2) 487-494) (Year: 2002).*
International Search Report (ISR) for PCT/JP2017/000023; I.A. fd: Jan. 4, 2017, dated Mar. 28, 2017 from the Japan Patent Office, Tokyo, Japan.
International Preliminary Report on Patentability (IPRP), Chapter I of the Patent Cooperation Treaty, including the Written Opinion for PCT/JP2017/000023; I.A. fd: dated Jan. 4, 2017, dated Jul. 31, 2018, by the International Bureau of WIPO, Geneva, Switzerland.
Fox, PT et al., "Nonoxidative glucose consumption during focal physiologic neural activity," Science. Jul. 22, 1988;241(4864):462-4, A, Assoc Adv Sci,, Washington, DC.

(Continued)

Primary Examiner — Michael Barker
Assistant Examiner — Randall O Winston
(74) Attorney, Agent, or Firm — Sterne, Kessler, Goldstein & Fox P.L.L.C.

(57) ABSTRACT

Provided is a material effective for improving the activity of nerves in the brain or for preventing or ameliorating brain dysfunction. An agent for activating astrocyte glucose metabolism, brain nerve cells activating agent, a brain hypofunction suppressing agent, a brain function improving agent, or an agent for preventing or ameliorating brain dysfunction comprising, as an active ingredient, one or more selected from the group consisting of hydrophobic solvent extracts of tien-cha, rooibos, grape and black tea.

2 Claims, 5 Drawing Sheets (56) References Cited

OTHER PUBLICATIONS

Bentourkia, M et al., "Comparison of regional cerebral blood flow and glucose metabolism in the normal brain: effect of aging," J Neurol Sci. Dec. 1, 2000;181(1-2):19-28, Elsevier, Amsterdam, Netherlands.

Herholz, K et al., "Discrimination between Alzheimer dementia and controls by automated analysis of multicenter FDG PET," Neuroimage. Sep. 2002;17(1):302-16, Academic Press, Orlando, FL.

Bélanger, M et al., "Brain energy metabolism: focus on astrocyte-neuron metabolic cooperation," Cell Metab. Dec. 7, 2011;14(6):724-38. doi: 10.1016/j.cmet.2011.08.016, Cell Press, Cambridge, MA.

Takahashi, S, "Energy Metabolism of neurons and astroglia," Cerebral Blood Flow and Metabolism 21:18-27 (2010).

Suzuki, A et al., "Astrocyte-neuron lactate transport is required for long-term memory formation," Cell. Mar. 4, 2011;144(5):810-23. doi: 10.1016/j.cell.2011.02.018, Elsevier, Amsterdam, Netherlands.

Zga, N et al., "Preparative purification of antiamyloidogenic stilbenoids from *Vitis vinifera* (Chardonnay) stems by centrifugal partition chromatography," J Chromatogr B Analyt Technol Biomed Life Sci. Apr. 1, 2009;877(10):1000-4. doi: 10.1016/j.jchromb.2009.02.026. Epub Feb. 13, 2009, Elsevier, Amsterdam, Netherlands.

Chaturvedula, VSP et al., "Isolation of Stigmasterol and β-Sitosterol from the dichloromethane extract of *Rubus suavissimus*," International Current Pharmaceutical Journal 2012, 1(9):239-242, Saki Publishing Club, Bangladesh.

Fiori, L et al., "Supercritical $CO_2$ extraction of oil from seeds of six grape cultivars: Modeling of mass transfer kinetics and evaluation of lipid profiles and tocol contents," The Journal of Supercritical Fluids 94: 71-80, (Oct. 2014); doi.org/10.1016/j.supflu.2014.06.021; Elsevier, Amsterdam, Netherlands.

Bravi, M et al., "Improving the extraction of α-tocopherol-enriched oil from grape seeds by supercritical $CO_2$. Optimisation of the extraction conditions," J Food Engineering 78(2):488-493, (Jan. 2007) doi: 10.1016/j.jfoodeng.2005.10.017.

Miyazawa, H et al., "Ninchisho Oyobi Kekkan Shinseibyo ni Taisuru Vitamin E no Kaizen Koka," Chapter 11 in Functional Food, 2010, vol. 3(3): 253-258, ISSN 1882-3971, Japan.

Urano, S et al, "Cognitive impairment caused by oxidative stress during aging, and its prevention by vitamin E," Vitamins, Mar. 2009, vol. 83, No. 2 pp. 85-93, ISSN 0006-386X, Vitamin Society of Japan, Kyoto, Japan.

Wang, Li-bo et al., "Latest research advances in bioactive components of sweet tea," Foods and oils and fats, vol. 2, (Feb. 10, 2007) College of Food Science, Southwest University, pp. 47-49 (with English abstract on p. 47).

Xu, Li-jia et al., Research Progress in Aspalathus Linearis, Drugs and Clinic vol. 28, No. 1, Jan. 30, 2013, pp. 74-77 (with English abstract on p. 74).

Xiong, Zhe, et al., Research progress of prevention and regulation of black tea on Alzheimer's disease, Journal of Food Safety and Quality, vol. 6, No. 4, Apr. 25, 2015, pp. 1219-1223 (including English abstract on p. 1219).

Extended European search report for EP Application No. 17743872.8, including the supplementary European search report and the European search opinion, dated Jul. 2, 2019, European Patent Office, Munich, Germany.

Inanami, O. et al., "The suppression of age-related accumulation of lipid peroxides in rat brain by administration of Rooibos tea (*Aspalathus linearis*)," Neurosci Lett. Aug. 18, 1995;196(1-2):85-8.

Hong, I.-S. et al., "Anti-oxidative effects of Rooibos tea (*Aspalathus linearis*) on immobilization-induced oxidative stress in rat brain," PLoS One. Jan. 21, 2014;9(1):e87061. doi: 10.1371/journal.pone.0087061. eCollection 2014.

\* cited by examiner

AGENT FOR ACTIVATING ASTROCYTE GLUCOSE METABOLISM

FIELD OF THE INVENTION

The present invention relates to a material for activating astrocyte glucose metabolism.

BACKGROUND OF THE INVENTION

The brain uses glucose as Its primary energy substrate and maintains the activity by using ATP produced through the metabolism thereof. The energy metabolism of brain nerve cells is important to maintain brain function and studies on the brain energy metabolism have been intensely conducted. The study using Positron Emission Tomography (PET) conducted by Fox et al. in 1988, measured brain glucose consumption ratio of human visual cortex, brain blood flow and brain oxygen consumption and revealed that increased brain functional activity by the visual stimulation enhances the brain glucose consumption and such a metabolism is anaerobic (Non Patent Literature 1). Accordingly, the brain glucose metabolism is postulated to be correlated with the brain functional activity. On the other hand, it is reported that brain glucose metabolism decreases with age or from the initial stage of Alzheimer's disease (Non Patent Literatures 2 and 3). Amelioration in the brain glucose metabolism is considered useful to prevent and relieve brain dysfunction associated with age and dementia such as Alzheimer's disease (Patent Literature 1).

Much of the brain glucose metabolism mechanism has been remained unknown so far. In 2000, a concept termed neurovascular unit, emphasizing the importance of intercellular network when thinking about the brain functions, was proposed. Trilateral network among neuron, brain microcirculation (microvasculature) and astrocyte is considered important, as is the case with the brain glucose metabolism. At present, astrocyte-neuron lactate shuttle hypothesis (ANLSH) is generally supported as the brain glucose metabolism mechanism despite various counter-evidences. According to this hypothesis, glucose is taken into cells mainly via glucose transporter 1 (GLUT1) of an astrocyte during the brain functional activity, metabolized in the glycolysis and converted to lactate. Subsequently, the lactate is transported exocytically by the works of monocarboxylate transporter 1 (MCT1) and monocarboxylate transporter 4 (MCT4) on the astrocyte and taken into a neuron. The neuron produces ATP using the lactate taken in as the energy substrate and becomes active by using it as an energy source (Non Patent Literature 4). Neuron itself can also take in glucose but selectively takes in lactate rather than glucose and uses it as the energy substrate (Non Patent Literature 5). Thus, the lactate supply by the astrocyte glucose metabolism is considered very important for activities and function maintenance of neurons.

Accordingly, in recent years, studies on the intracerebral lactate have been intensely conducted. Non Patent Literature 6 reports that a mouse in which MCT1 or MCT4, a monocarboxylate transporter present in an astrocyte, is knocked out has reduced memory formation, and lactate administration into the brain of the mouse improves the reduction in the memory formation, while glucose administration is not effective to improve the reduction in the memory formation, and based on these findings the lactate supply from an astrocyte to neurons is considered very important for forming memory.

On the other hand, Patent Literature 1 describes a method for ameliorating mental activities of a patient by administering a substance which ameliorates the insulin sensitivity in the brain and increases glucose use. However, according to Non Patent Literature 6, the increased glucose use by neurons in the brain is insufficient for amelioration of the brain function and the increase in lactate production by an astrocyte and the lactate supply from an astrocyte to a neuron are considered important.

Patent Literature 2 discloses that Galloylated proanthocyanidins derived from a grape seed extract is used for treating a neurodegenerative disease. Patent Literature 3 discloses that an unfermented rooibos extract by a mixed solution of water-alcohol is used to prevent and/or treat a dementia. Patent Literature 4 discloses that a caspase-9 activity inhibition composition containing an *Aspalathus linearis* (rooibos) extract or a black tea extract is used as a pharmaceutical preparation to treat or prevent neuropathy in which the presence of caspase-9 is involved. Patent Literatures 5 and 6 disclose that the protein glycation reaction in vivo is a factor of the function decline with age such as dementia and hot-water extracts of rooibos, tien-cha and black tea inhibited the protein glycation reaction or promoted the zymolysis of an advanced glycation end product.

(Patent Literature 1) JP-A-2002-532416
(Patent Literature 2) JP-A-2011-520814
(Patent Literature 3) JP-A-2012-501990
(Patent Literature 4) JP-A-2004-307443
(Patent Literature 5) JP-A-2013-253072
(Patent Literature 6) JP-A-2014-118406
(Non Patent Literature 1) Science, 241:462-464, 1988
(Non Patent Literature 2) J Neurol Sci, 181(1-2):19-28, 2000
(Non Patent Literature 3) Neuroimage, 17:302-316, 2002
(Non Patent Literature 4) Cell Metabo, 14(6):724-738, 2011
(Non Patent Literature 5) Cerebral Blood Flow and Metabolism, 21:18-27, 2010
(Non Patent Literature 6) Cell, 144:810-823, 2011

SUMMARY OF THE INVENTION

The present invention provides an agent for activating astrocyte glucose metabolism comprising, as an active ingredient, one or more selected from the group consisting of hydrophobic solvent extracts of tien-cha, rooibos, grape and black tea.

The present invention also provides a brain nerve cell activating agent comprising, as an active ingredient, one or more selected from the group consisting of hydrophobic solvent extracts of tien-cha, rooibos, grape and black tea.

The present invention also provides a brain hypofunction suppressing agent comprising, as an active ingredient, one or more selected from the group consisting of hydrophobic solvent extracts of tien-cha, rooibos, grape and black tea.

The present invention also provides a brain function improving agent comprising, as an active ingredient, one or more selected from the group consisting of hydrophobic solvent extracts of tien-cha, rooibos, grape and black tea.

The present invention also provides an agent for preventing or ameliorating brain dysfunction comprising, as an active ingredient, one or more selected from the group consisting of hydrophobic solvent extracts of tien-cha, rooibos, grape and black tea.

DETAILED DESCRIPTION OF THE INVENTION

All Patent Literatures, Non Patent Literatures and other publications cited herein are incorporated by reference in their entirety.

The present invention relates to the provision of a material effective for improving the activity of nerves in the brain or for preventing or ameliorating the brain dysfunction caused with age or by dementia such as Alzheimer's disease.

The present inventors searched for effective ingredients for activating the glucose metabolism in the brain and found that a hydrophobic solvent extract of tien-cha, rooibos, grape or black tea has an effect for activating astrocyte glucose metabolism and is effective for activating the activity of nerves in the brain, for improving or suppressing decline in brain functions, or for preventing or ameliorating brain dysfunction.

The present invention can provide a material which has good astrocyte glucose metabolism activation effect and is effective for improving an energy supply to neurons in the brain and improving the activity of nerves in the brain. The present invention accordingly enables improvement in brain function, suppression of decline in brain function, or prevention or amelioration of the brain dysfunction caused with age or by dementia such as Alzheimer's disease.

The "astrocyte glucose metabolism activation" used herein preferably refers to the metabolism activity to convert glucose to lactate by an astrocyte or improvement in the lactate production activity by an astrocyte. The change in the astrocyte glucose metabolism level can be evaluated by measuring changes in the amount of glucose uptake or the amount of lactate production by an astrocyte. The change in the amount of glucose uptake or the amount of lactate production by an astrocyte can be measured by culturing astrocytes in glucose-containing medium and comparing glucose amounts or lactate amounts in the medium before and after the culture. Alternatively, the change in the astrocyte glucose metabolism level can be evaluated by culturing astrocytes in glucose-containing medium and measuring oxygen consumption or by measuring pH change in the medium by the lactate produced. The pH change of the medium can be measured by measuring the change in the hydrogen ion concentration of the medium. The measurements of the oxygen consumption by cells and the pH change of the medium can be carried out using, for example, an extracellular flux analyzer (Seahorse Bioscience).

Alternatively, the change in the astrocyte glucose metabolism level can be evaluated by measuring the expression levels of genes or proteins relating to the glucose uptake, the conversion of glucose to lactate or the lactate transport by the astrocyte. Examples of the gene or protein relating to the glucose uptake, the conversion of glucose to lactate or the lactate transport by the astrocyte include glucose transporter 1 (GLUT1), monocarboxylate transporter 1 (MCT1), monocarboxylate transporter 4 (MCT4) and genes encoding them, and homologues, paralogues and orthologues of these genes. The measurement of expression level of these genes or proteins can employ methods typically used in the art. For example, the gene expression level can be measured by quantitative RT-PCR method, RNase protection assay, Northern blot analysis, RNA sequence analysis by next-generation sequencer or DNA microarray analysis, and the measurement of the protein expression level can be measured by a typical immunoassay such as RIA method, ELISA, bioassay method, proteome or Western blotting.

Examples of the "brain function" used herein include memory, learning, thinking, attention or perception, speech, spatiotemporal perception, orientation, cognition or comprehensive judgment ability of other abstract events, and performance ability, with memory or learning ability, comprehensive judgment ability and performance ability being preferable. Thus, the "brain hypofunction suppression" and "brain function improvement" used herein preferably mean, for memory, learning, thinking, attention or perception, speech, spatiotemporal perception, orientation, cognition or comprehensive judgment ability of other abstract events, and performance ability, to suppress decline in these abilities and to improve these abilities. Further, the "brain dysfunction" used herein preferably refers to memory disorder, learning disability, thinking disability caused with age, by injuries or dementia such as Alzheimer's disease or vascular dementia, or impairment of cognitive or comprehensive judgment ability, or to a symptom or sign of dementia such as Alzheimer's disease or vascular dementia.

The "non-therapeutic" used herein means a concept which does not include medical practice, in other words, a concept which does not include surgery, treatment or diagnosis on a person, more specifically, a concept which does not include a method wherein a medical practitioner or a person instructed by a medical practitioner does not perform a surgery, treatment or diagnosis on a person.

The "prevention" used herein refers to prevent, suppress or delay the development of a disease, symptom or condition on an individual, or to reduce a risk of the development of a disease, symptom or condition on an individual. Further, the "amelioration" used herein refers to change a disease, symptom or condition for the better, to prevent, suppress or delay the aggregation of a disease, symptom or condition, or to reverse, prevent, suppress or delay the progression of a disease, symptom or condition.

The tien-cha used in the present invention is a leaf of the family Rosaceae Tien-cha (*Rubus suavissimus* S. Lee).

The rooibos used in the present invention is the family Fabaceae rooibos (*Aspalathus linearis* L.). Further, the grape used in the present invention refers to plants belonging to the genus *Vitis* of the family Vitaceae, and examples include European grape (*Vitis vinifera* L.), American grape (*Vitis labrusca*), muscadine (*Vitis rotundifolia*), Amur grape (*Vitis amurensis*), wild vine (*Vitis coignetiae*) and crossbreds thereof, with *Vitis vinifera* L. being preferable. Grapes are roughly classified according to the peel colors into three groups of "red", "black" and "green (white)", but in the present invention all of red, black and green (white) can be used and the combinations thereof can also be used. Red grape can be preferably used. Any parts of the above plants can be used such as the entire tree, entire plant, a leaf (including a lamina and a petiole), bark, xylem, a branch, a fruit, peel, a seed, a flower (including a petal and an ovary), a root, a rhizome or the like of a plant, or combinations thereof. Preferable parts to be used are a leaf of rooibos and a fruit or peel of the grape, with a fruit containing the skin and seeds being more preferable.

The black tea used in the present invention is a fermented product of leaf of the family Theaceae tea (*Camellia sinensis*).

In the present invention, the above tien-cha, rooibos, grape or black tea may be used as it is or by cutting, crushing, pulverizing or squeezing, or may be used in the form of dry product thereof. Dry products are preferably used. The dry product may also be cut, crushed, pulverized or powdered.

The tien-cha extract, rooibos extract, grape extract or black tea extract used in the present invention may be an extract obtained by extracting the above tien-cha, rooibos, grape or black tea as it is or by extracting from the dried, cut, crushed, pulverized or squeezed plant described above, but the extract is preferably from the dried product of the above tien-cha, rooibos, grape or black tea, or from the cut, crushed, pulverized or powdered product of the above dried product.

The extraction means for obtaining the above extract can be a typical means such as solid-liquid extraction, squeeze extraction, liquid-liquid extraction, immersion, decoction, leaching, reflux extraction, Soxhlet extraction, ultrasonic extraction, microwave extraction, or stirring. These extraction means may be used in combination. For example, the immersion and solid-liquid extraction may be combined with the liquid-liquid extraction, or the solid-liquid extraction may be carried out in combination with stirring to cut the extraction time.

Examples of the solvent for extracting the above extracts include hydrophobic solvents (including low polar solvents and non-polar solvents) such as chain ethers such as diethyl ether; saturated or unsaturated hydrocarbons such as pentane and hexane; aromatic hydrocarbons such as benzene and toluene; halogenated hydrocarbons such as dichloromethane, chloroform, dichloroethane, and carbon tetrachloride; carbon dioxide and supercritical carbon dioxide; edible oils such as rapeseed oil and soybean oil; fats or oils such as diacylglycerol (DAG), medium chain fatty acid oils, squalane, and squalene; and mixtures thereof. Of the above extraction solvents, pentane, hexane, supercritical carbon dioxide, edible oils, and fats or oils are preferable, with hexane being more preferable.

The amount of the solvent used for extraction is preferably 1 to 100 mL per g of the plant (on a dry mass basis). The extraction conditions are not limited as long as sufficient extraction can be carried out. Typically, the extraction is carried out for a longer time with the solvent having a lower temperature and for a shorter time with the solvent having a higher temperature. For example, the extraction time is preferably 1 hour or more, more preferably 12 hours or more, whereas it is preferably 2 months or less, more preferably 4 weeks or less. Further, the extraction temperature is, for example, preferably 0° C. or more, more preferably 5° C. or more, whereas it is preferably a temperature lower than the solvent boiling point but may be about room temperature. Examples of the preferable extraction conditions include 3 days to 4 weeks at 15 to 40° C., but are not limited thereto and can be suitably selected by a person skilled in the art.

The conditions for supercritical carbon dioxide extraction preferably have an amount of carbon dioxide to be used of from 10 to 200 g per g of the plant (on a dry mass basis), from 7.5 to 50 MPa, 40 to 100° C., from 1 to 24 hours. About 1% by mass of ethanol may be added as needed.

The extracts obtained by the above procedure may also be purified as needed by the purification treatment typically used for the production of plant extracts such as those using organic solvent precipitation, centrifugation, ultrafiltration membrane, high-performance liquid chromatograph, column chromatograph, liquid-liquid distribution, gel filtration separation, or activated charcoal.

The extracts obtained by the above procedure may also be used in the form of an extract liquid or a fraction thereof singly or in mixture, or as they are, or as a diluted solution diluted using a suitable solvent, or may be used as prepared in the form of a concentrated extract, dry powder or paste by concentration or freeze-drying. Alternatively, the concentrated extract, dry powder or paste may also be used as diluted when used with a solvent such as water, ethanol, propylene glycol, butylene glycol, water-ethanol mixed solution, water-propylene glycol mixed solution, or water-butylene glycol mixed solution. Alternatively, the concentrated extract, dry powder or paste may also be used as encapsulated in a vesicle such as liposome or a microcapsule.

In the present invention, the hydrophobic solvent extract of tien-cha, rooibos, grape or black tea may be used singly or in combinations of two or more. Preferably, a hexane extract of tien-cha, rooibos, grape or black tea, or combinations of two or more selected from the group consisting of these hexane extracts.

The hydrophobic solvent extract of tien-cha, rooibos, grape, or black tea has the effect for activating astrocyte glucose metabolism and the effect for improving the brain functions decreased by disorders (Examples 1 to 3 described later). The activation of astrocyte glucose metabolism increases the activity of neurons in the brain when a larger amount of lactate to be the energy substrate is supplied to neurons in the brain (for example, see Non Patent Literatures 1 and 4) and also improves the brain functions (for example, cognitive function such as memory, learning, and comprehensive judgment ability, and performance ability) or suppresses decline therein (for example, see Non Patent Literatures 2 and 6). Accordingly, the hydrophobic solvent extract of tien-cha, rooibos, grape or black tea is effective for activating astrocyte glucose metabolism, improving an energy supply to neurons in the brain, activating brain nerve cells, improving the brain functions or suppressing decline in brain functions, and further preventing or ameliorating brain dysfunction.

Thus, in an embodiment, the present invention provides an agent for activating astrocyte glucose metabolism comprising, as an active ingredient, at least one selected from the group consisting of hydrophobic solvent extracts of tien-cha, rooibos, grape and black tea. Further, the present invention provides an agent for improving an energy supply to neurons in the brain, brain nerve cell activating agent, a brain function improving agent, a brain hypofunction suppressing agent, or an agent for preventing or ameliorating brain dysfunction, comprising, as an active ingredient, at least one selected from the group consisting of hydrophobic solvent extracts of tien-cha, rooibos, grape and black tea.

In another embodiment, the present invention provides use of at least one selected from the group consisting of hydrophobic solvent extracts of tien-cha, rooibos, grape and black tea for producing an agent for activating astrocyte glucose metabolism, an agent for improving an energy supply to neurons in the brain, a brain nerve cell activating agent, a brain function improving agent, a brain hypofunction suppressing agent, or an agent for preventing or ameliorating brain dysfunction.

In an embodiment, the above agents can essentially comprise at least one selected from the group consisting of hydrophobic solvent extracts of tien-cha, rooibos, grape and black tea.

In still another embodiment, the present invention provides use of at least one selected from the group consisting of hydrophobic solvent extracts of tien-cha, rooibos, grape and black tea for activating astrocyte glucose metabolism, improving an energy supply to neurons in the brain, activating brain nerve cells, improving brain function, suppressing brain hypofunction, or preventing or ameliorating brain dysfunction.

In further another embodiment, the present invention provides at least one selected from the group consisting of hydrophobic solvent extracts of tien-cha, rooibos, grape and black tea for use in activating astrocyte glucose metabolism, improving an energy supply to neurons in the brain, activating brain nerve cells, improving brain function, suppressing brain hypofunction, or preventing or ameliorating brain dysfunction.

The above use of the present invention may be a therapeutic use or a non-therapeutic use. Examples of the therapeutic use include uses on a person diagnosed with dementia, or on a person who has severe cognitive function impairment and is interfered with daily life. Examples of the non-therapeutic use include uses on a person who is not interfered with daily life by decline in brain functions but needs brain function improvement, brain hypofunction suppression, or brain dysfunction prevention, such as a person with mild cognitive impairment (MCI), a person considered to have decline in brain functions such as memory, learning or cognitive function, or a person who desires further improvement in memory and learning ability. Additionally, for example, the non-therapeutic use is to provide, not as medical practice, others with the hydrophobic solvent extract of tien-cha, rooibos, grape or black tea for administration or consumption by claiming the effects of the above brain function improvement, brain hypofunction suppression or brain dysfunction prevention.

In the present invention, the hydrophobic solvent extract of tien-cha, rooibos, grape or black tea can be used on both human and non-human animals. Examples of the non-human animal include non-human mammals and birds, and examples of the non-human mammal include anthropoids, other primates, mice, rats, hamsters, dogs, cats, and companion animals.

In the present invention, the hydrophobic solvent extract of tien-cha, rooibos, grape or black tea can be used as the active ingredient in pharmaceutical products, quasi drugs or food and drink products to impart functions for activating astrocyte glucose metabolism, improving an energy supply to neurons in the brain, activating brain nerve cells, improving brain function, suppressing brain hypofunction, or preventing or ameliorating brain dysfunction.

The above pharmaceutical products (including quasi drugs) are pharmaceutical products for activating astrocyte glucose metabolism, improving an energy supply to neurons in the brain, activating brain nerve cells, improving brain function, suppressing brain hypofunction, or preventing or ameliorating brain dysfunction and comprises, as an active ingredient, at least one selected from the group consisting of hydrophobic solvent extracts of tien-cha, rooibos, grape and black tea for such functions. Further, the pharmaceutical products may comprise, as long as the functions of the active. ingredient are not lost, a pharmaceutically acceptable carrier, other active ingredients, and a pharmacological component as needed.

The administration form of the above pharmaceutical products (including quasi drugs) may be either oral administration or parenteral administration. The dosage form of the pharmaceutical products is not particularly limited but may be a dosage form which can be orally or parenterally administered, and, for example, may be any of injections, suppositories, inhalers, percutaneous absorbents, various external agents, tablets, capsules, granules, powders, liquids, or syrups, and preparations in these various dosage forms can be prepared in accordance with a routine method by suitably combining the hydrophobic solvent extract of tien-cha, rooibos, grape or black tea with a pharmaceutically acceptable carrier (for example, an excipient, a binder, an extender, a disintegrator, a surfactant, a lubricant, a dispersant, a buffer, a preservative, a flavor, a perfume, a coating agent, and a diluent) and other pharmacological components.

The content (on a dry product basis) of the hydrophobic solvent extract of tien-cha, rooibos, grape or black tea in the above pharmaceutical products (including quasi drugs) is not particularly limited, but is preferably, in the total mass, 0.01% by mass or more, more preferably 0.1% by mass or more, further preferably 1.0% by mass or more, still preferably 10% by mass or more, and preferably 95% by mass or less, more preferably 80% by mass or less, further preferably 60% by mass or less. Further, examples of the content include 0.01 to 95% by mass, from 0.01 to 80% by mass, from 0.01 to 60% by mass, from 0.1 to 95% by mass, from 0.1 to 80% by mass, from 0.1 to 60% by mass, from 1.0 to 95% by mass, from 1.0 to 80% by mass, from 1.0 to 60% by mass, from 10% by mass to 95% by mass, from 10% by mass to 80% by mass, and from 10% by mass to 60% by mass.

The above food and drink products are to provide the function for activating astrocyte glucose metabolism, improving an energy supply to neurons in the brain, activating brain nerve cells, improving brain function, suppressing brain hypofunction, or preventing or ameliorating brain dysfunction and comprise, as an active ingredient, at least one selected from the group consisting of hydrophobic solvent extracts of tien-cha, rooibos, grape and black tea for such functions. The food and drink products have a concept of activating astrocyte glucose metabolism, improving an energy supply to neurons in the brain, activating brain nerve cells, improving brain function, suppressing brain hypofunction, or preventing or ameliorating brain dysfunction, and encompass food and drink products for the sick and food with health claims such as food and drink products with nutrient function claims, food and drink products for specified health uses, and food and drink products for function claims on which the above concept is labelled as needed. These food and drink products may be provided together with function claims such as "increase memory", "prevent memory loss and language loss", "increase the ability to speech, judge, understand or think", "prevent or ameliorate age-related decline in brain functions", or "relieve or prevent delusion, wandering or hallucination symptoms due to decline in cognitive function".

The form of the above food and drink products can be solid, semi-solid or liquid (for example, a drink). Examples of the food and drink products include breads, noodles, rices, confectionery such as cookies, jellies, dairy products, soups, frozen foods, instant foods, starch processed products, processed fish meat products, other processed foods, seasonings, nutrition supplement foods, and drinks such as teas, coffee drinks, fruit drinks, carbonated drinks, and jelly-like drinks, as well as raw materials thereof. Alternatively, the food and drink products may be supplement in the form of a preparation for oral administration such as tablets, capsules, granules, powders, liquids and solutions, or syrups.

The food and drink products can be prepared in accordance with a routine method by suitably combining the hydrophobic solvent extract of tien-cha, rooibos, grape or black tea with any additives acceptable for food and drink materials or food and drink products (for example, a solvent, a softener, an oil, an emulsifier, a preservative, a perfume, a sweetener, a stabilizer, a coloring agent, a ultraviolet absorber, an antioxidant, a moisturizing agent, a thickener, a bonding agent, a dispersant, or a wetting agent).

The content (on a dry product basis) of the hydrophobic solvent extract of tien-cha, rooibos, grape or black tea in the above food and drink products is not particularly limited, but is preferably, in the total mass, 0.0001% by mass or more, more preferably 0.001 by mass or more, further preferably 0.01% by mass or more, further more preferably 0.1% by mass or more, and still preferably 1% by mass or more, and preferably 50% by mass or less, more preferably 20% by mass or less, further preferably 10% by mass or less. Further, examples of the content include from 0.0001 to 50% by mass, from 0.0001 to 20% by mass, from 0.0001 to 10 by mass, from 0.001 to 50%; by mass, from 0.001 to 20% by mass, from 0.001 to 10 by mass, from 0.01 to 50% by mass, from 0.01 to 20% by mass, from 0.01 to 10% by mass, from 0.1 to 50% by mass, from 0.1 to 20% by mass, from 0.1 to 10% by mass, from 1 to 50% by mass, from 1 to 20% by mass, and from 1 to 10% by mass.

In still another embodiment, the present invention provides a method for activating astrocyte glucose metabolism of a subject. Additionally, the present invention provides a method for improving an energy supply to neurons in the brain of a subject. Further, the present invention provides a method for activating brain nerve cells of a subject. Furthermore, the present invention provides a method for improving brain function or suppressing brain hypofunction of a subject. Additionally, the present invention provides a method for preventing or ameliorating brain dysfunction of a subject. The methods comprise administering an effective dose of at least one selected from the group consisting of hydrophobic solvent extracts of tien-cha, rooibos, grape and black tea to a subject. The methods may be therapeutic methods or non-therapeutic methods.

Examples of the subject in the above methods include animals in desire or need of activating astrocyte glucose metabolism, improving an energy supply to neurons in the brain, activating brain nerve cells, improving brain function, suppressing brain hypofunction, or preventing or ameliorating brain dysfunction. Examples of the animal are not particularly limited as long as an animal has the brain but include human and non-human animals described above, with human being more preferable.

The method for activating astrocyte glucose metabolism, the method for improving an energy supply to neurons in the brain, and the method for activating brain nerve cells of the present invention may be in vitro methods. Examples of the subject in the case of the in vitro method include brain tissues or cultured astrocytes derived from the human or non-human animals described above.

The administration effective dose in the above methods can be an amount which can achieve the astrocyte glucose metabolism activation of a subject. Preferably, the effective dose is the amount at which the astrocyte glucose metabolism of an administered group can be significantly increased statistically when compared with a non-administered group. Further preferably, the effective dose is the amount which can increase, in cultured astrocytes, the glucose metabolism of an administered group by 105% or more, preferably by 110% or more, more preferably by 120% or more, of a non-administered group. Alternatively, the effective dose is the amount which can statistically significantly increase the brain activity of an administered group when compared with a non-administered group. The brain activity is measured by functional MRI, PET, Single-photon emission computed tomography (SPECT), near-infrared spectroscopy (NIRS), or magnetoencephalography (MEG).

In the present invention, the administration dose and dosage regimen of the hydrophobic solvent extract of tien-cha, rooibos, grape or black tea may be suitably determined by a person skilled in the art in accordance with species, body weight, sex, age, conditions or other factors of a subject. The administration dose of the hydrophobic solvent extract (on a dry product basis) of tien-cha, rooibos, grape or black tea of the present invention is, but not limited thereto, preferably 1 mg or more, more preferably 5 mg or more, further preferably 15 mg or more, and preferably 10 g or less, more preferably 5 g or less, further preferably 1 g or less, daily per adult. The above dose is preferably, for example, administered once, or in a divided dose of twice or three times or more daily, for several weeks to several months continuously.

The present invention also encompasses the following substances, production methods, purposes of use, and methods as exemplary embodiments. However, the present invention is not limited to these embodiments.

[1] An agent for activating astrocyte glucose metabolism comprising, as an active ingredient, one or more selected from the group consisting of hydrophobic solvent extracts of tien-cha, rooibos, grape and black tea.

[2] A brain nerve cell activating agent comprising, as an active ingredient, one or more selected from the group consisting of hydrophobic solvent extracts of tien-cha, rooibos, grape and black tea.

[3] A brain hypofunction suppressing agent comprising, as an active ingredient, one or more selected from the group consisting of hydrophobic solvent extracts of tien-cha, rooibos, grape and black tea.

[4] A brain function improving agent comprising, as an active ingredient, one or more selected from the group consisting of hydrophobic solvent extracts of Lien-cha, rooibos, grape and black tea.

[5] An agent for preventing or ameliorating brain dysfunction comprising, as an active ingredient, one or more selected from the group consisting of hydrophobic solvent extracts of tien-cha, rooibos, grape and black tea.

[6] An agent for improving an energy supply to neurons in the brain comprising, as an active ingredient, one or more selected from the group consisting of hydrophobic solvent extracts of tien-cha, rooibos, grape and black tea.

[7] Use of one or more selected from the group consisting of hydrophobic solvent extracts of tien-cha, rooibos, grape and black tea for producing an agent for activating astrocyte glucose metabolism.

[8] Use of at least one selected from the group consisting of hydrophobic solvent extracts of tien-cha, rooibos, grape and black tea for producing a brain nerve cell activating agent.

[9] Use of at least one selected from the group consisting of hydrophobic solvent extracts of tien-cha, rooibos, grape and black tea for producing a brain hypofunction suppressing agent.

[10] Use of at least one selected from the group consisting of hydrophobic solvent extracts of tien-cha, rooibos, grape and black tea for producing a brain function improving agent.

[11] Use of at least one selected from the group consisting of hydrophobic solvent extracts of tien-cha, rooibos, grape and black tea for producing an agent for preventing or ameliorating brain dysfunction.

[12] Use of at least one selected from the group consisting of hydrophobic solvent extracts of tien-cha, rooibos, grape and black tea for producing an agent for improving an energy supply to neurons in the brain.

[13] At least one selected from the group consisting of hydrophobic solvent extracts of tien-cha, rooibos, grape and black tea for use in activating astrocyte glucose metabolism.

[14] At least one selected from the group consisting of hydrophobic solvent extracts of tien-cha, rooibos, grape and black tea for use in activating brain nerve cells.

[15] At least one selected from the group consisting of hydrophobic solvent extracts of tien-cha, rooibos, grape and black tea for use in suppressing brain hypofunction.

[16] At least one selected from the group consisting of hydrophobic solvent extracts of tien-cha, rooibos, grape and black tea to be used improving the brain functions.

[17] At least one selected from the group consisting of hydrophobic solvent extracts of tien-cha, rooibos, grape and black tea for use in preventing or ameliorating brain dysfunction.

[18] At least one selected from the group consisting of hydrophobic solvent extracts of tien-cha, rooibos, grape and black tea for use in improving an energy supply to neurons in the brain.

[19] Use of at least one selected from the group consisting of hydrophobic solvent extracts of tien-cha, rooibos, grape and black tea for activating astrocyte glucose metabolism.

[20] Use of at least one selected from the group consisting of hydrophobic solvent extracts of tien-cha, rooibos, grape and black tea for activating brain nerve cells.

[21] Use of at least one selected from the group consisting of hydrophobic solvent extracts of tien-cha, rooibos, grape and black tea for suppressing brain hypofunction.

[22] Use of at least one selected from the group consisting of hydrophobic solvent extracts of Lien-cha, rooibos, grape and black tea for improving the brain functions.

[23] Use of at least one selected from the group consisting of hydrophobic solvent extracts of tien-cha, rooibos, grape and black tea for preventing or ameliorating brain dysfunction.

[24] Use of at least one selected from the group consisting of hydrophobic solvent extracts of Lien-cha, rooibos, grape and black tea for improving an energy supply to neurons in the brain.

[25] A method for activating astrocyte glucose metabolism of a subject, comprising administering an effective dose of at least one selected from the group consisting of hydrophobic solvent extracts of tien-cha, rooibos, grape and black tea to the subject.

[26] A method for activating brain nerve cells of a subject, comprising administering an effective dose of at least one selected from the group consisting of hydrophobic solvent extracts of tien-cha, rooibos, grape and black tea to the subject.

[27] A method for suppressing brain hypofunction of a subject, comprising administering an effective dose of at least one selected from the group consisting of hydrophobic solvent extracts of tien-cha, rooibos, grape and black tea to the subject.

[28] A method for improving the brain functions of a subject, comprising administering, an effective dose of at least one selected from the group consisting of hydrophobic solvent extracts of tien-cha, rooibos, grape and black tea to the subject.

[29] A method for preventing or ameliorating brain dysfunction of a subject, comprising administering an effective dose of at least one selected from the group consisting of hydrophobic solvent extracts of tien-cha, rooibos, grape and black tea to the subject.

[30] A method for improving an energy supply to neurons in the brain of a subject, comprising administering an effective dose of at least one selected from the group consisting of hydrophobic solvent extracts of tien-cha, rooibos, grape and black tea to the subject.

[31] In the [1], [7], [13], [19], and [25], the astrocyte glucose metabolism activation is preferably improved expression of one or more genes selected from the group consisting of GLUT1 gene, MCT1 gene and MCT4 gene in an astrocyte.

[32] In the [5], [11], [17], [23], and [29], the brain dysfunction is preferably memory disorder, learning disability and thinking disability caused with age, by injuries or dementia, or impairment of cognitive or comprehensive judgment ability, or a symptom or sign of dementia.

[33] In the [1] to [12], the agent is preferably a preparation for oral administration. [34] In the [13] to [18], the use is preferably a use as a medicament for activating astrocyte glucose metabolism, activating brain nerve cells, suppressing brain hypofunction, improving brain function, improving brain function, preventing or ameliorating brain dysfunction, or improving an energy supply to neurons in the brain.

[35] In the [34], the medicament is preferably an oral drug.

[36] In the [19] to [24], the use is preferably a non-therapeutic use.

[37] In the [36], the hydrophobic solvent extract of tien-cha, rooibos, grape or black tea is preferably used in the form of supplement.

[38] In the [25] to [30], the administration is preferably oral administration.

[39] In the [1] to [38], preferably,
the tien-cha is a leaf of *Rubus suavissimus* S. Lee,
the rooibos is a leaf of *Aspalathus linearis* L.,
the grape is a fruit of *Vitis vinifera* L. containing the skin and seeds, and
the black tea is a fermented product of leaf of *Camellia sinensis*.

[40] In the [1] to [39], hydrophobic solvent extract of tien-cha, rooibos, grape or black tea is preferably an extract extracted using a solvent selected from the group consisting of pentane, hexane, supercritical carbon dioxide, an edible oil and a fat or oil, and more preferably a hexane extract.

[41] In the [25] to [30], the subject is preferably an animal in desire or need of activating astrocyte glucose metabolism, improving an energy supply to neurons in the brain, activating brain nerve cells, improving brain function, suppressing brain hypofunction, or preventing or ameliorating brain dysfunction.

EXAMPLES

Hereinafter, the present invention is further described in detail in reference to Examples, but not limited thereto.

Production Example Preparation of Extracts (Tien-Cha Extract)
100 mL of hexane or 99.5% ethanol was added to 10 g of a dried leaf product (tien-cha, purchased from Cha Oroshi Sohonpo) of the family Rosaceae Tien-cha (*Rubus suavissimus* S. Lee) and the product was allowed to stand and immersed at room temperature for 8 to 11 days. Subsequently, the extraction residue was removed by filtration, followed by distilling under reduced pressure and drying the obtained extract liquid to thereby obtain 50.8 mg of a hexane extract and 424.1 mg of an ethanol extract.

(Rooibos Extract)
100 mL of hexane or 99.5% ethanol was added to 10 g of a dried leaf product (rooibos tea, purchased from Cha Oroshi Sohonpo) of the family Fabaceae rooibos (*Aspalathus linearis* L.) and the product was allowed to stand and immersed at room temperature for 8 to 11 days. Subsequently, the extraction residue was removed by filtration, followed by distilling under reduced pressure and drying the obtained extract liquid to thereby obtain 26.6 mg of a hexane extract and 97.7 mg of an ethanol extract.

(Grape Extract)
100 g of fresh fruits (Chilean Red Globe, purchased from Mizuumeya) of the family Vitaceae grape (*Vitis vinifera* L.) was freeze-dried without removing the skin and seeds to thereby obtain 20.01 g of a dried fruit product. 100 mL of hexane or 99.5% ethanol was added to 10 g of the dried product and the product was allowed to stand and immersed at room temperature for 9 to 12 days. Subsequently, the extraction residue was removed by filtration, followed by distilling under reduced pressure and drying the obtained extract liquid to thereby obtain 9.2 mg of a hexane extract and 3.23 mg of an ethanol extract.

(Black Tea Extract)
100 mL of hexane or 99.5% ethanol was added to 10 g of a fermented tea (black tea, purchased from Cha Oroshi Sohonpo) having leaves of the family Theaceae tea (*Camellia sinensis*) as the raw material and the tea was allowed to stand and immersed at room temperature for 8 to 11 days. Subsequently, the extraction residue was removed by filtration, followed by distilling under reduced pressure and drying the obtained extract liquid to thereby obtain 21.5 mg of a hexane extract and 217.6 mg of an ethanol extract.

Example 1 Astrocyte Glucose Metabolism Activation

In a cell, glucose is metabolized in the glycolysis, converted to lactate and exocytically released, and the exocytically released lactate reduces the pH at cell peripheral environment. In the present Example, a pH change of an astrocyte culture was measured to evaluate the impact of a test substance on the astrocyte glucose metabolic capacity. For the measurement of pH changes, an extracellular flux analyzer (XF96; Seahorse Bioscience) was used. This system measures hydrogen ion concentration changes of a cell culture by a luminescence method and calculates an extracellular acidification rate (ECAR). An increase in ECAR reflects the improvement in the glucose metabolic capacity of a cell. When ECAR is increased by the addition of a test substance, the test substance is a substance which activates the astrocyte glucose metabolic capacity.

For the test substances, the hexane extracts and ethanol extracts of tien-cha, rooibos, grape or black tea prepared in the above Production Example were used. These extracts were respectively dissolved in 99.5% ethanol in such a way that a concentration was 1% (w/v) and used as samples. For a positive control, 1 mM of metformin (an agent for activating glucose metabolism (AMPK activation agent): Sigma) was used.

Primary culture astrocytes (from SD rat fetal brain; Cosmo Bio) were cultured using astrocyte medium (Cosmo Bio) in an incubator at 5% $CO_2$, 95% air, and 37° C. The cells were subcultured using trypsin-EDTA (Gibco), and the third subculture cells were used. The third subculture astrocytes were inoculated in a 96-well plate in a concentration of 5,000 cells/well and cultured for 8 days in the astrocyte medium, which was subsequently replaced with DMEM/F12 serum-free medium (Gibco). On the day before the test, each sample (a final concentration of 0.002% in terms of the test substance) was added to the medium. For a control, test substance-free medium was used.

After the sample was added and cultured overnight, the medium was replaced with DMEM medium for XF96 measurement (Seahorse) to measure ECAR. The measurement, with 1 loop of 9 min (mix; 3 min, time delay; 2 min, measure; 4 min), of 6 loops were made, subsequently glucose (a final concentration 5 mM; Wako Pure Chemistry) or DMEM medium for XF96 measurement was added to the medium, and the measurement was further continued to 12 loops. When the ECAR value before glucose was added (the value at the 6th loop) was 100%, a change rate of ECAR after glucose was added was calculated and an area under concentration curve (AUC) from 6 to 12 loops was determined. As in the formula below, the AUC difference between the glucose-added group and the glucose-free group (XF96 measurement medium-added group) was defined as the glucose metabolic capacity of each test substance-added group.

(Glucose metabolic capacity)=(Glucose-added group AUC)−(Glucose-free group AUC)

With the glucose metabolic capacity of the test substance-free group (control) being 1, a relative value of the glucose metabolic capacity of each test substance-added group was determined. The results are shown in FIGS. 1 to 4. In the astrocytes of the medium to which the hexane extract of tien-cha, rooibos, grape or black tea was added, elevated ECAR increases by glucose were confirmed, thereby verifying that these hexane extracts have the activation effect of astrocyte glucose metabolism (FIGS. 1 to 4; A). On the other hand, in all of tien-cha, rooibos, grape or black tea, the ethanol extracts did not have an ECAR increase effect (FIGS. 1 to 4; B).

Example 2 Improved Expression of Glucose Metabolism-Related Genes in Astrocytes

The hexane extract of tien-cha, rooibos, grape or black tea was investigated for the impact on expression of the genes, glucose transporter 1 (GLUT1), monocarboxylate transporter 1 (MCT1) and monocarboxylate transporter 4 (MCT4), which are the astrocyte glucose metabolism-related genes.

The hexane extracts of tien-cha, rooibos, grape or black tea prepared in the above Production Example were respectively dissolved in 99.5% ethanol in such a way that a concentration was 1% (w/v) and used as samples. For a control, test substance-free medium was used.

Primary culture astrocytes (Cosmo Bio) were inoculated in a 6-well plate in a concentration of 480,000 cells/well and cultured for 8 days in the astrocyte medium (Cosmo Bio), which was subsequently replaced with DMEM/F12 serum-free medium (Gibco). On the day before the test, each sample (a final concentration of 0.002% in terms of the test substance) was added to the medium and cultured overnight. Subsequently, the medium was removed and washed with PBS, and all RNA was extracted from the cells using a RNeasy Mini Kit (Qiagen). cDNA was synthesized from all the extracted RNA using High Capacity RNA-to-cDNA kit (Applied Biosystems). Quantitative PCR, with the obtained cDNA as a template, was carried out using Taqman Fast Universal PCR Master Mix (Applied Biosystems) and ABI Prism 7700 system (Applied Biosystems). Each of the gene expression levels was normalized using a GAPDH gene expression level. With each gene expression level in the control group being 1, a relative expression level of each gene in the hexane extract-added group was determined.

The results are shown in FIGS. 5 to 8. In the astrocytes of the medium to which the hexane extract of tien-cha, rooibos, grape or black tea was added, the expression of one or more of GLUT1, MCT1 and MCT4 genes were increased. Thus, the hexane extracts of tien-cha, rooibos, grape or black tea were confirmed to have promoted the glucose take in or lactate transport by astrocytes, and thereby activating the cell glucose metabolism.

Example 3 Novel Object Recognition Test

Novel object recognition test is a test for evaluating the cognitive function exploiting the novelty-seeking nature of mouse. For the test, C57BL/6J mice (male, 5 weeks of age) (CLEA Japan, Inc.) were used. The mice were kept at room temperature 22±2° C., a humidity 55±10%, lighting 12-hour cycle (7:00 a.m. to 7:00 p.m.), during which food and water were available ad libitum. The animals were divided into 3 groups of (I) control group, (II) glucose metabolism inhibition group, and (III) glucose metabolism inhibition+tien-cha group. As test meals, the glucose metabolism inhibition+tien-cha group was allowed to consume a feed (corn oil 10%, casein 20%, cellulose 4%, mineral 3.5%, vitamin 1%, potato starch 61%) to which 0.5 mass % of a tien-cha hexane extract prepared in the same method as in the above Production Example was added, and the control group and the glucose metabolism inhibition group were allowed respectively to consume a tien-cha extract-free feed (corn oil 10%, casein 20%, cellulose 4%, mineral 3.5%, vitamin 1%, potato starch 61.5%).

On week 4 of the test meal consumption, a guide cannula (length 4 mm) was inserted into the mouse left hippocampus (A: −3.1, L: 2.5, V: −1.3 mm) under isoflurane anesthesia using a brain stereotactic fixture to ensure a drug administration route into the brain. The guide cannula was fixed to the head with a dental cement.

On week 5 of the test meal consumption, the novel object recognition test was carried out. In the test, an habituation trial, an training trial, and a test trial were carried out for 3 consecutive days (24-hour intervals). More specifically, on the first day, the mice were put in a plastic cage in which no object was disposed and acclimated for 10 minutes (habituation trial). On the following day, 2 different objects were disposed in the cage, in which the mice were allowed to freely explore for 5 minutes (training trial). Twenty four hours later, one of the objects in the case was replaced with a new object, in which the mice were allowed to freely explore for 5 minutes (test trial). One hour before the training trial, drugs were administered into the mouse brain. 0.1 µL of a Ringer's solution of glycogenolysis enzyme inhibitor (1,4-dideoxy-1,4-amino-D-arabinitol hydrochloride; 10 mM) (Sigma) which inhibits the brain glucose metabolism was administered to the glucose metabolism inhibition group and the glucose metabolism inhibition tien-cha group. 0.1 µL of a Ringer's solution was administered to the control, group. The drug was administered by inserting an injection cannula (length 7 mm) into the guide cannula fixed to the head of the mouse and using a microsyringe therefrom.

The number of times the mice contacted each object (the number of times the mice poked the object in the nose) during the training trial and the test trial was counted as the number of exploration, and the proportion (%) of the number of exploration to each object in relative to the total number of exploration to the objects was calculated. The number of exploration to the novel object reflects the memory or learning ability of the mouse; more specifically, when the memory or learning ability is normal, the number of exploration to the novel object during the retention trial increases, whereas when the memory or learning ability is impaired, the novel object is not distinguished from the familiar object thereby the number of exploration to the novel object decreases.

Figure 1:
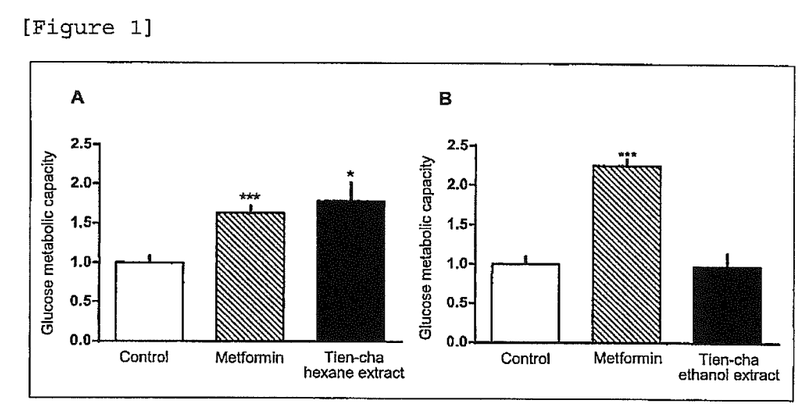
FIG. 1 shows the astrocyte glucose metabolism activation effect by a tien-cha extract. A: Hexane extract, error bar=±standard error (n=5 to 6). B: Ethanol extract, error bar=±standard error (n=4 to 6). *p<0.05, ***p<0.001 (t-test, vs control).
Figure 2:
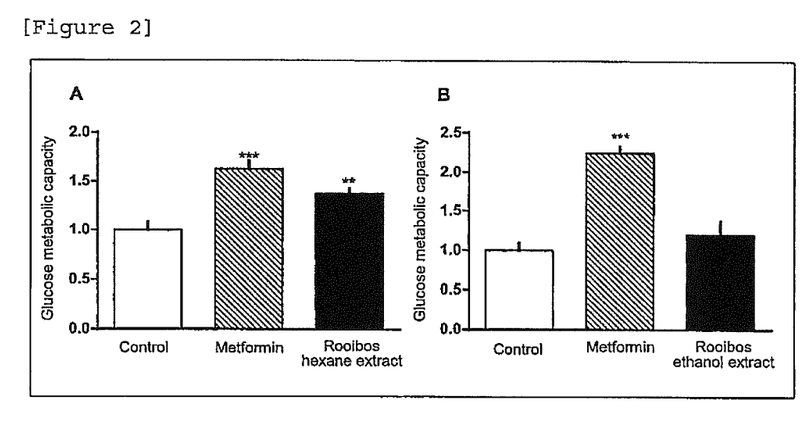
FIG. 2 shows the astrocyte glucose metabolism activation effect by a rooibos extract. A: Hexane extract, error bar=±standard error (n=5 to 6). B: Ethanol extract, error bar=±standard error (n=4 to 5). p<0.005, *p<0.001 (t-test, vs control).
Figure 3:
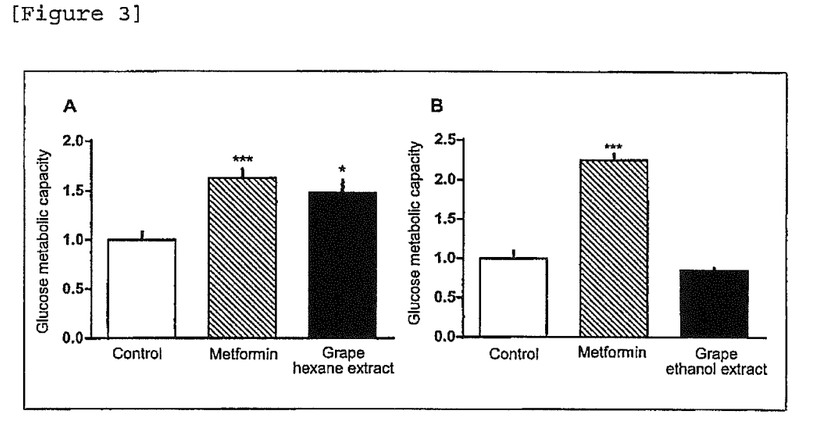
FIG. 3 shows the astrocyte glucose metabolism activation effect by a grape extract. A: Hexane extract, error bar=±standard error (n=4 to 5). B: Ethanol extract, error bar=±standard error (n=4 to 6). *p<0.05, ***p<0.001 (t-test, vs control).
Figure 4:
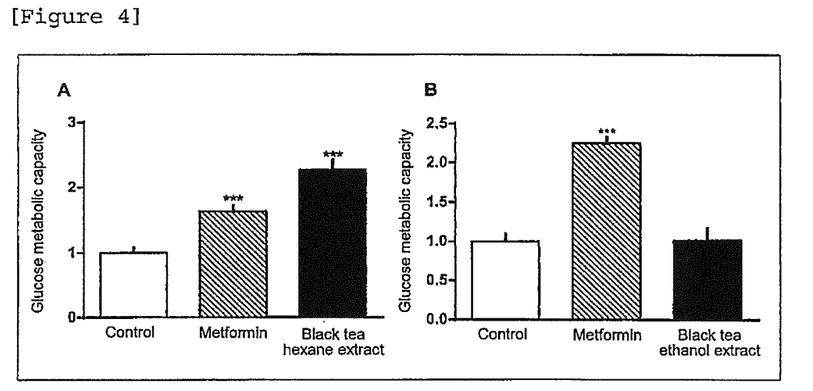
FIG. 4 shows the astrocyte glucose metabolism activation effect by a black tea extract. A: Hexane extract, error bar=±standard error (n=5 to 6). B: Ethanol extract, error bar=±standard error (n=4 to 5). ***p<0.001 (t-test, vs control).
Figure 5:
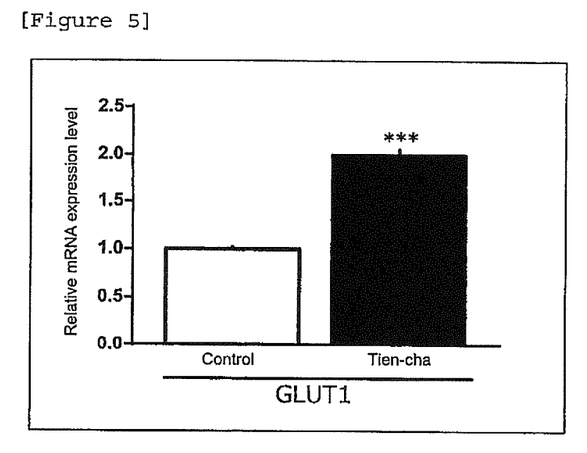
FIG. 5 shows improved expression of the GLUT1 gene by a tien-cha hexane extract. Error bar±standard error (n=4). ***p<0.001 (t-test, vs control).
Figure 6:
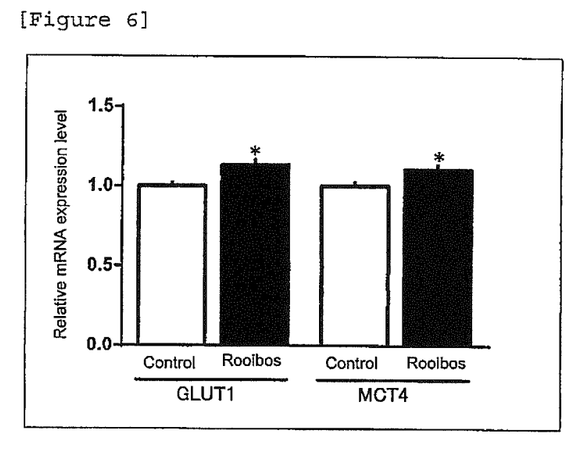
FIG. 6 shows improved expression of the GLUT1 gene and MCT4 gene by a rooibos hexane extract. Error bar=±standard error (n=4). *p<0.05 (t-test, vs control).
Figure 7:
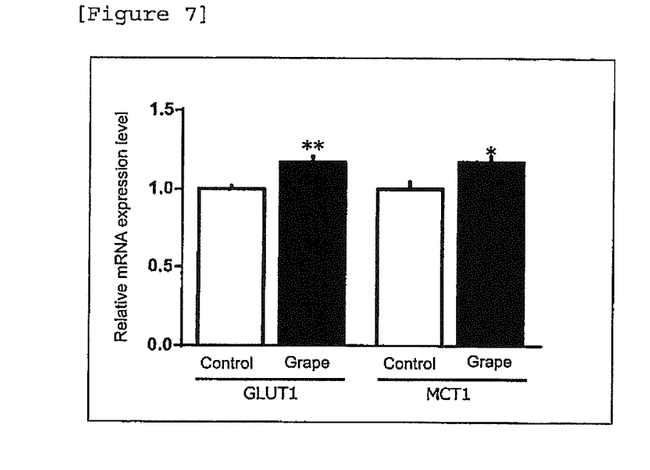
FIG. 7 shows improved expression of the GLUT1 gene and MCT1 gene by a grape hexane extract. Error bar=±standard error (n=4). p<0.05, **p<0.005 (t-test, vs control).
Figure 8:
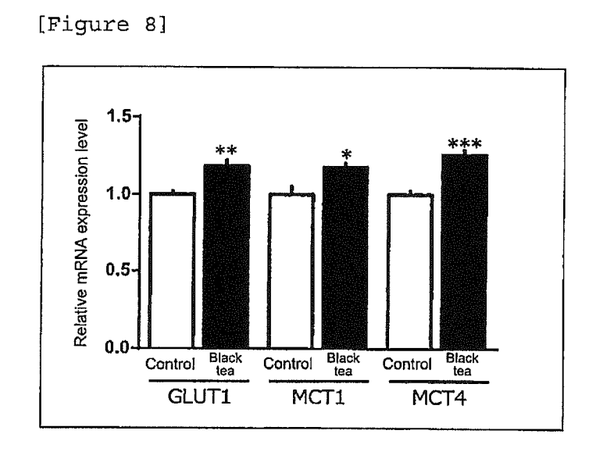
FIG. 8 shows improved expression of the GLUT1 gene, MCT1 gene and MCT4 gene by a black tea hexane extract. Error bar=±standard error (n=4). *p<0.05, p<0.005, *p<0.001 (t-test, vs control).
Figure 9:
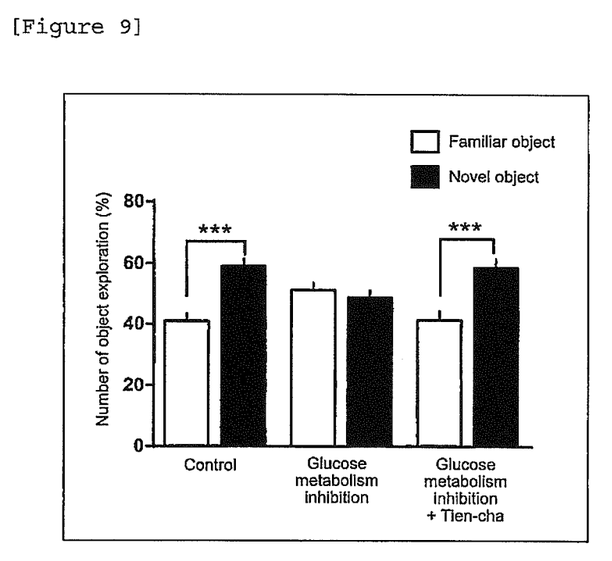
FIG. 9 shows the amelioration in the novel object recognition ability in a mouse by a tien-cha extract administration. Error bar=±standard error 6 to 8). ***p<0.001 (One-way ANOVA Tukey test).

The test results are shown in FIG. 9. In the control group, the proportion of the number of exploration to the novel object is significantly higher than the familiar object, verifying that the memory and learning functions are normal. On the other hand, in the glucose metabolism inhibition group, there is no difference in the numbers of exploration between the familiar object and the novel object, verifying that the memory or learning function was impaired. In contrast, the proportion of the number of exploration to the novel object in the glucose metabolism inhibition+tien-cha group was significantly higher than the known object, and was about the same when compared with the control group. From these findings, it was verified that the memory or learning function impairment caused by the glucose metabolism inhibition was prevented or ameliorated by the tien-cha extract administration.

What is claimed is:

1. A method for ameliorating brain dysfunction in a subject in need thereof, the method comprising administering an effective dose of a hydrophobic solvent extract of at least one selected from the group consisting of tien-cha, rooibos, and black tea to the subject in need thereof,
wherein the hydrophobic solvent is selected from the group consisting of pentane, hexane, supercritical carbon dioxide, an edible oil, a fat and an oil, and
wherein the brain dysfunction is a memory or learning dysfunction.

2. The method according to claim 1, wherein the solvent is hexane.

\* \* \* \* \*